(12) United States Patent
Koopman

(10) Patent No.: US 10,456,505 B2
(45) Date of Patent: Oct. 29, 2019

(54) BIODEGRADABLE EXTRAVASCULAR STENT

(71) Applicant: Mallinckrodt Pharma IP Trading D.A.C., Hazelwood, MO (US)

(72) Inventor: Jacob Laurens Koopman, Leiderdorp (NL)

(73) Assignee: Mallinckrodt Pharma IP Trading D.A.C., Dublin (IE)

( * ) Notice: Subject to any disclaimer, the term of this patent is extended or adjusted under 35 U.S.C. 154(b) by 0 days.

(21) Appl. No.: 15/400,628

(22) Filed: Jan. 6, 2017

(65) Prior Publication Data
US 2017/0143875 A1    May 25, 2017

Related U.S. Application Data

(63) Continuation of application No. 13/147,969, filed as application No. PCT/EP2010/051421 on Feb. 5, 2010, now abandoned.

(30) Foreign Application Priority Data

Feb. 6, 2009 (EP) .................................. 091523357

(51) Int. Cl.
A61L 31/04 (2006.01)
A61L 31/14 (2006.01)
A61L 31/16 (2006.01)

(52) U.S. Cl.
CPC ............ *A61L 31/046* (2013.01); *A61L 31/041* (2013.01); *A61L 31/042* (2013.01); *A61L 31/14* (2013.01); *A61L 31/16* (2013.01); *A61L 2300/418* (2013.01)

(58) Field of Classification Search
None
See application file for complete search history.

(56) References Cited

U.S. PATENT DOCUMENTS 6,113,948 A * 9/2000 Heath .................. A61L 24/106
424/489

OTHER PUBLICATIONS

Stooker, W; et al; "Perivenous application of fibrin glue reduces early injury to the human saphenous vein graft wall in an ex vivo model" European Journal of Cardio-thoracic Surgery, 21, 212-217, 2002 (Year: 2002).*
Parang, Pirouz; Arora, Rohit; "Coronary vein graft disease: Pathogenesis and prevention" Canadian Journal of Cardiology, 25, e57-e62, 2009 (Year: 2009).*

* cited by examiner

*Primary Examiner* — David W Berke-Schlessel

(57) ABSTRACT

The present invention relates to extravascular supports. In particular, to extravascular supports which are used in vein grafting. More in particular, it relates to extravascular supports which are biodegradable.

13 Claims, 1 Drawing Sheet

BIODEGRADABLE EXTRAVASCULAR STENT

CROSS REFERENCE

This application is continuation of U.S. application Ser. No. 13/147,969, filed on Oct. 10, 2011, which is a national stage entry of PCT/EP10/51421, filed on Feb. 5, 2010, the disclosure of which is herein incorporated by reference in its entirety.

FIELD OF THE INVENTION

The present invention relates to extravascular supports. In particular, to extravascular supports which are used in vein grafting. More in particular, it relates to biodegradable extravascular supports.

BACKGROUND OF THE INVENTION

Aorta-coronary and peripheral vein grafts are known to have a high failure rate due to occlusive complications in the graft as a result of an accelerated atherosclerosis process that is designated as vein graft disease. A prominent factor promoting vein graft disease is endothelial cell damage as a result of over distention of the vein graft because of the high arterial pressure it becomes exposed to. The accelerated atherosclerosis process that eventually results in the occlusion of the graft is strongly enhanced in hypercholesterolemic patients.

Extravascular supports or stents have been shown to improve the outcome of graft procedures because they prevent overextension and can ameliorate the arterialisation process (balanced increase in smooth muscle cells located in the medial layer of the vessel wall of the vein graft) that is needed to adapt the vein graft to the arterial pressure. Studies have indicated that if properly supported by an extravascular stent (artificial tubing surrounding the graft vessel), vein graft thickening and atherosclerosis is strongly inhibited (Mehta et al. (1998) Nature Med. 4(2), 235). Thus far. stents have been used that have to be custom-adjusted during surgery, that interfere with X-ray graft imaging and remain in the patient long after the graft has adopted to its new environment and outgrown the need for support. The ideal extravascular support fits all grafts with minimal effort, is biodegradable, imaging compatible, porous and elastic (Hinrichs et al (1994) Biomaterials 15(2), 83). Fibrin polymers fit all these criteria (Stooker et al. (2002) Eur. J. Cardiothorac. Surg. 21(2), 212) and preliminary results show that following the treatment of vein grafts with a liquid fibrinogen/thrombin sealant, vessel wall thickening was decreased (Stooker et al. (2002) Eur. J. Cardiothorac. Surg. 21(2): 212).

Fibrinogen and thrombin are natural blood proteins that play a pivotal role in blood clotting. At the end of the cascade that causes blood to clot, thrombin triggers the conversion of soluble fibrinogen into an insoluble fibrin network. This network stops the bleeding and provides a matrix for cells involved in wound repair. Commercially available fibrin-based products that mimic this last step in the clotting cascade are currently used to treat topical bleeding and to promote tissue adhesion. Fibrin is a fully biodegradable matrix that supports the natural healing process and in addition to supporting in vivo haemostatic plug formation, is also involved in tissue repair and remodeling.

A disadvantage of these fibrin glues is that they consist of two separate solutions containing fibrinogen and thrombin respectively, which have to be mixed directly on the wound, to prevent a premature reaction of the components. These fibrinogen and thrombin components have to be stored separately as frozen liquids or as lyophilized powders that need to be reconstituted before use. Such glues are described in, for example, Stooker et al. (2002) Fur. J. Cardiothorac. Surg. 21(2): 212 and Stooker et al. (2003) Ann. Thor. Surg. 76:1533.

The fibrinogen glue is viscous and completely homogenously mixing with the non viscous thrombin solution is often not achieved before fibrin polymer formation starts. As a result, a non-homogenous fibrin polymer is formed which influences visco-elastic properties of the fibrin. These features make the controlled use (e.g. even vein graft coating) of fibrin glues for extravascular support difficult. Furthermore, the available fibrin glues use high ratios of thrombin/fibrinogen (5-20 1U thrombin/mg fibrinogen) which increases the risk of "free" active thrombin passing through the vessel wall into the blood stream (Dascombe et al. (1997) Thromb. Haemost. 78 (2), 947), where it may cause intravascular coagulation. Thrombin applied as a liquid—in particular when applied at high concentrations—poses therefore a safety risk.

DETAILED DESCRIPTION OF THE INVENTION

Figure 1:
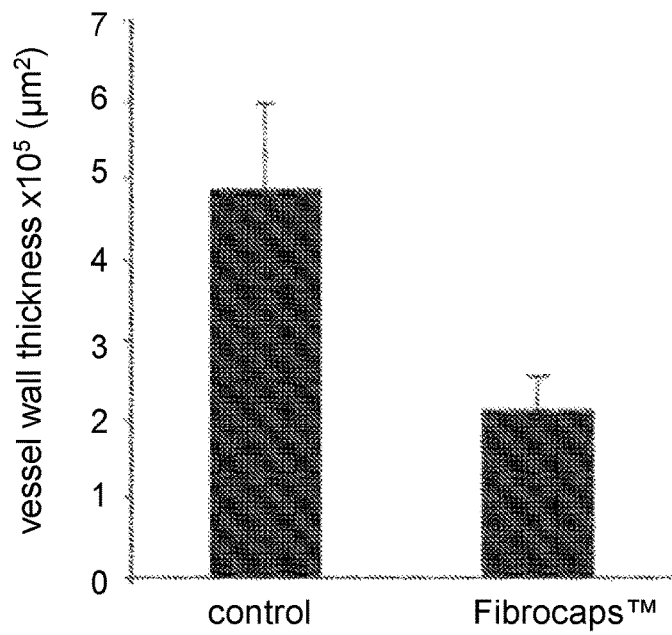
FIG. 1 Vessel wall thickening after 4 weeks.

The present invention relates to an extravascular fibrin polymer support or stent which is obtainable by coating a venous graft with a dry powder formulation of fibrinogen and a fibrinogen activator, such as thrombin, and to a method for producing such a stent.

In the present context, 'stent' refers to a support or matrix for a blood vessel, in particular a vein. The vein is surrounded by such a stent, typically to prevent or treat vein graft disease or overextension of the vein.

One advantage of an extravascular stem according to the invention is that the dry powder formulation can be stored as a pre-mixed blend at ambient temperatures and can be applied in a variety of ways. Another advantage is that the fibrin polymer of the stem will be homogenous with respect to fibrin polymer structure, because the fibrinogen and thrombin are pre-mixed.

Yet another advantage of the extravascular fibrin polymer stem prepared by using a dry powder formulation of fibrinogen and thrombin over liquid sealants is that the dry powder formulation polymerizes in the limited amount of fluid that is naturally present at the outside of the vessel wall. Polymerization of fibrinogen in a small volume results in a stronger fibrin matrix (Glidden et al. (2000) Clin. Appl. Thromb. Hemost. 6(4), 226) that surrounds the vessel. Hence, a superior extravascular support is obtained as compared to using diluted liquids.

Yet another advantage is that dry powder formulations are more easily localized than the liquid fibrin glues. Dry powder formulations can therefore be administered locally e.g. by wrapping the vein to be transplanted in powder, thereby only applying to the outer surface of the vessel to be treated.

Another advantage is that by using dry powder formulations of fibrinogen and thrombin for the preparation of extravascular stents, the amount of thrombin used may be much lower than when using liquid fibrin glues. The risk of "free" active thrombin passing through the vessel wall into the blood is considerably reduced, thereby for example reducing the risk of intravascular coagulation by thrombin passing the vascular wall and the effect that thrombin may have in promoting proliferation and migration of smooth muscle cells in the vascular wall.

Any dry powder formulation of fibrinogen and thrombin may be used to obtain the extravascular stent according to the invention provided that it comprises fibrinogen and thrombin in such a way that pre-mature reactions are avoided. For example, the fibrinogen and thrombin may be in separate microparticles in the dry powder formulation. The amount of fibrinogen and thrombin used will depend on the circumstances, for example on the length of the vein to be coated. Therefore, the amount of fibrinogen may be between 10 mg and 10 g per dose of dry powder formulation. The amount of thrombin may be between 0.1 and 10000 IU per dose of dry powder formulation. Preferably, the dry powder formulation preferably contains 1-30% w/w fibrinogen per gram of dry powder formulation and 0.1-1000 or 1 to 750 or 5 to 500 or 10 to 300 or 20 to 250 IU of thrombin per gram dry powder formulation. IUs are as defined in Whitton et al. (2005) Thromb Haemost. 93(2)261-6.

The fibrinogen and the thrombin may be isolated from blood from human donors or be made by recombinant DNA technology in cultured cells or transgenic animals or plants. This includes both modified and optimized fibrinogen and thrombin which have retained their activity. They may be full-length or any active fragment thereof. Both wild-type and variants of these proteins may be used. For example, for fibrinogen this includes variants which have risen through genetic polymorphisms, differences in glycosylation and phosphorylation, (partial) proteolysis of the carboxyterminal part of the Act-chain and alternative splicing.

The powder may comprise particles or microparticles, which may be solid or hollow, such as in the case of microcapsules. Preferably, the powder is free flowing. Microparticles comprising fibrinogen or thrombin may be prepared by methods known in the art, for example as described in WO 92/18164, WO 96/09814, WO 96/18388 or WO 97/44015. These spray-drying and associated particle manipulation processes enable the production of microcapsules with defined size distribution. The microcapsules may have any suitable size. In one embodiment, the microcapsules mean size are between 2 and 50 micrometer in diameter. In another embodiment, the microcapsules are between 5 and 50 micrometer in diameter. In yet another embodiment, they are between 10 and 50 micrometer in diameter. In yet another embodiment, they are between 20 and 50 micrometer in diameter. The microparticles may be produced reproducibly. In one embodiment, at least 90% or more have a mass median particle of up to 50 micrometer.

Typically, excipients are present during spray-drying, in particular carbohydrate excipients, such as monosaccharides, disaccharides and polysaccharides, including fructose, galactose, glucose, lactose, maltose, starches and sucrose. In a preferred embodiment, trehalose, lactose, sucrose or mannitol is present. Most preferably, trehalose is present. Other excipients, such as HSA, coagulation factors, bulking agents, may also be present, for example in order to improve dispersability, physical and chemical stability, flowability and consistence of the dry powder formulation.

Although the preferred method of preparation of the dry powder formulation includes spray drying, other drying techniques may also be used to prepare the dry powder formulation. Microparticles may be sterilised, if necessary or desired, using techniques known in the art.

A suitable example of a formulation which can be used to prepare stents according to the invention is the commercial preparation Fibrocaps® (ProFibrix. Leiden, The Netherlands), which comprises stabilised and separately spray-dried microparticles of fibrinogen and thrombin. This dry powder Formulation is fully active after storage for 1 year at 40° C. and even 3 months' incubation at 60° C. does not result in a decrease of activity. The preparation of the Fibrocaps® formulation is described in U.S. Pat. No. 6,113,948. It is mentioned that the formulation may be used in wound therapy or surgical repair. There is no indication that the formulation can be used to prevent or treat overextension of blood vessels, a completely different field.

In another aspect, the present invention relates to a method for producing an extravascular fibrin polymer stent, which method comprises applying to a segment or the whole of a vein a dry powder formulation of fibrinogen and a fibrinogen activator, such as thrombin, as described before. A vein coated with a dry powder formulation of fibrinogen and fibrinogen activator, such as thrombin, and a vein coated with fibrin polymer obtained by applying a dry powder formulation of fibrinogen and a fibrinogen activator, such as thrombin, to the vein arc also part of the present invention. The vein may be any kind of vein which needs to be protected against (further) overextension or which needs support, for instance a varicose vein. In a preferred embodiment, the vein is a venous graft. In one embodiment, the powder formulation is applied before the venous graft is introduced in the human or animal body. In another embodiment, the powder formulation is applied after the venous graft has been introduced in the human or animal body. The dry powder formulation polymerizes in the limited amounts of bodily fluids which are naturally present at the outside of the vessel wall, thus forming an extravascular stent. A superior extravascular support is obtained as compared to using diluted liquids, since polymerization of fibrinogen in a small volume results in a stronger fibrin matrix (Glidden et al. (2000) Clin. Appl. Thromb. Hemost. 6(4), 226).

The person skilled in the art will understand that instead of thrombin any other activator of fibrinogen may be used, such as for example snake venom thrombin-like enzymes like reptilase.

EXAMPLES

Example 1 Testing of Fibrocaps for Extravascular Stent in a Mouse Vein Graft Model Dry powder formulation Fibrocaps™, containing human plasma derived fibrinogen (6% w/w based on Fibrocaps) (ZLB, Marburg, Germany) and thrombin (500 IU/gram of Fibrocaps) (SNBTS, Glasgow, UK) was tested in transgenic mice that are susceptible to cholesterol induced atherosclerosis, according to the method described by Lardenoye et al. (Circulation Res. (2002) October 4, 577). In brief, the animals are fed a high-fat diet containing 0.5% cholate to improve intestinal cholesterol uptake and suppress bile-acid synthesis. This leads to increased plasma cholesterol levels.

After 4 weeks of chow or HFC 0.5%, mice are anesthetized with Hypnorm (Bayer, 25 mg/kg) and Dormicum (Roche, 25 mg/kg). The procedure used for vein grafts was similar to that described by Zou et al. (Am. J. Pathol. (1998) 153. 1301).

In brief, the right common carotid artery was dissected free from its surrounding from the bifurcation at the distal end toward the proximal end. The artery was cut in the middle and a cuff placed at the end on both sides. Next, both ends of the artery were everted over the cuffs and ligated with an 8.0 silk ligature. The vena cava was harvested and grafted between the two ends of the carotid artery by sleeving the end of the vein over the artery cuff and ligating them together with an 8.0 silk suture. In these mice a venous interposition was placed in the carotid artery as a model for vein grafting in these mice, Fibrocaps™ powder was applied to the outside of the graft before it was exposed to arterial pressure.

Histological Assessment of Vein Graft Lesions.

At euthanasia, mice were anesthetized with Hypnorm/Dormicum. The thorax was opened and mild pressure-perfusion (100 mm Hg) with 3.75% formaldehyde in 0.9% NaCl (wt/vol) for 10 minutes was performed by cardiac puncture. After perfusion, the vein graft was harvested, fixed overnight in 3.7% formaldehyde in phosphate buffered saline, and paraffin embedded.

To quantify the effect of hypercholesterolemia on intimal thickening in murine vein grafts, mice on either a chow diet or HFC 0.5% diet were euthanized 28 days after surgery. Six equally spaced cross-sections throughout the center of the graft were used in all mice to quantify intimal lesions. Using image analysis software (Qwin, Leica), total vessel wall cross sectional area, luminal area, and outer vessel wall circumferential area was measured between the lumen and the adventitia.

Statistics

All data are presented as mean±SEM. Overall comparisons between groups were performed with the Kruskal-wallis test. If a significant difference was found, groups were compared with their control using Mann-Whitney rank sum test. Values of $P<0.05$ were regarded significant.

Results

Figure 2A:
FIG. 2A shows a vein graft supported by Fibrocaps™.
Figure 2B:
FIG. 2B shows a control vein graft.

A dense fibrin matrix was formed around the vein graft and 4 weeks hereafter the vein grafts were analyzed for increased wall thickness and atherosclerotic lesions. The results in Figure I show that after application of the Fibrocaps™, a limited increase in vessel wall thickness is observed whereas the thickening of the vessel wall in grafts without extravascular support is much higher. FIG. 2A shows that the vessel wall thickening in the mice treated with Fibrocaps™ is limited due to reduced proliferation of smooth muscle cells in the vessel wall vein graft in combination with reduced foam cells accumulation. In mice without extravascular support (FIG. 2B) there are atherosclerotic lesions present in the neointima of the vein graft that ultimately may lead to thrombotic events that occlude the graft.

These results indicate that Fibrocaps™ is active as a biodegradable extravascular support of vein graft during bypass surgery to treat coronary and/or peripheral vein graft disease.

What is claimed is:

1. A method for preventing or treating vein graft disease, the method comprising:
    applying, to a segment or to the whole of a vessel wall of a vein, a dry powder formulation comprising fibrinogen and a fibrinogen activator to prepare an extravascular fibrin polymer stent, wherein the dry powder formulation is applied to an outer surface of the vein, and wherein after 4 weeks, the vessel wall has a thickness less than if the extravascular stent had not been applied to the vein.

2. The method of claim 1, wherein the fibrinogen or the fibrinogen activator is in a recombinant or a variant form.

3. The method of claim 1, wherein the dry powder formulation further comprises a carbohydrate selected from the group consisting of trehalose, sucrose, and lactose.

4. The method of claim 1, wherein the dry powder formulation is obtained by spray-drying.

5. The method of claim 1, wherein the dry powder formulation comprises the fibrinogen and fibrinogen activator in separate particles or microparticles.

6. The method of claim 1, wherein the vein is a venous graft.

7. The method of claim 1, wherein the fibrinogen activator is thrombin or reptilase.

8. The method of claim 7, wherein the dry powder formulation comprises 10 mg-1 g of fibrinogen and 0.1-10000 IU of thrombin per dose of dry powder formulation.

9. The method of claim 7, wherein the dry powder formulation comprises 1-30% w/w of fibrinogen and 0.1-1000 IU of thrombin per gram of dry powder formulation.

10. The method of claim 1, wherein the dry powder formulation of fibrinogen and fibrinogen activator is applied to the vein before implanting the extravascular fibrin polymer stent into the patient.

11. The method of claim 9, wherein the dry powder formulation comprises 6-30% w/w of fibrinogen and 250-1000 IU of thrombin per gram of dry powder formulation.

12. The method of claim 11, wherein the dry powder formulation comprises 6% w/w of fibrinogen and 500 IU of thrombin per gram of dry powder formulation.

13. The method of claim 1, wherein any increase in vessel wall thickness of the extravascular fibrin polymer stent is less than a thickening of the vessel wall in grafts without extravascular support.

* * * * *